United States Patent
Ajay et al.

(10) Patent No.: US 9,993,828 B2
(45) Date of Patent: Jun. 12, 2018

(54) PARTICLE PRECIPITATOR

(75) Inventors: Kemal Ajay, Mount Waverley (AU); Brian Alexander, Wantima (AU)

(73) Assignee: Garrett Thermal Systems Limited, Bracknell Berkshire (GB)

( * ) Notice: Subject to any disclaimer, the term of this patent is extended or adjusted under 35 U.S.C. 154(b) by 936 days.

(21) Appl. No.: 13/582,839

(22) PCT Filed: Mar. 3, 2011

(86) PCT No.: PCT/AU2011/000237
§ 371 (c)(1),
(2), (4) Date: Nov. 13, 2012

(87) PCT Pub. No.: WO2011/106840
PCT Pub. Date: Sep. 9, 2011

(65) Prior Publication Data
US 2013/0192341 A1    Aug. 1, 2013

(30) Foreign Application Priority Data

Mar. 5, 2010   (AU) ................................ 2010900937

(51) Int. Cl.
*B03C 3/34*       (2006.01)
*G08B 17/113*    (2006.01)
(Continued)

(52) U.S. Cl.
CPC ............... *B03C 3/34* (2013.01); *B03C 3/08* (2013.01); *B03C 3/366* (2013.01); *G01N 15/06* (2013.01);
(Continued)

(58) Field of Classification Search
CPC ......... B03C 3/34; B03C 3/366; B01D 53/323; G01N 15/06; G08B 17/10; G08B 17/113
See application file for complete search history.

(56) References Cited

U.S. PATENT DOCUMENTS 3,704,572 A * 12/1972 Gourdine .................. B03C 3/12
                                                                96/58
3,705,478 A * 12/1972 Vaneldik .................. G01N 1/24
                                                                174/16.1
(Continued)

FOREIGN PATENT DOCUMENTS

DE    102008002857 A1    11/2009
JP         04-227075 A      8/1992
(Continued)

OTHER PUBLICATIONS

Jaworek, Anatol, Andrzej Krupa, and Tadeusz Czech. "Modern electrostatic devices and methods for exhaust gas cleaning: A brief review." Journal of Electrostatics 65.3 (2007): 133-155.*

(Continued)

*Primary Examiner* — Lisa Caputo
*Assistant Examiner* — Punam Roy
(74) *Attorney, Agent, or Firm* — Schwegman Lundberg & Woessner, P.A.

(57) ABSTRACT

A particle separation system for separating particles in an airflow upstream of a detection chamber in an aspirating smoke detector is disclosed. The particle separation system includes an airflow path for directing the airflow from an inlet to an outlet. The airflow path includes a first airflow path section in a first direction and a second airflow path section in a second direction, the first and second directions being different relative to each other. The airflow path also includes at least one electrically charged surface such that the airflow undergoes electrostatic precipitation as it traverses the airflow path. A method of separating particles in an airflow upstream of a detection chamber in an aspirating smoke detector is also disclosed.

6 Claims, 3 Drawing Sheets

(51) Int. Cl.
*G01N 15/06* (2006.01)
*G08B 17/10* (2006.01)
*B03C 3/08* (2006.01)
*B03C 3/36* (2006.01)
*B01D 53/32* (2006.01)

(52) U.S. Cl.
CPC ............ *G08B 17/10* (2013.01); *G08B 17/113* (2013.01); *B01D 53/323* (2013.01); *B03C 2201/24* (2013.01)

(56) References Cited

U.S. PATENT DOCUMENTS

| | | | | |
|---|---|---|---|---|
| 5,002,720 | A * | 3/1991 | Berggren | G01T 3/00 250/370.03 |
| 5,160,510 | A | 11/1992 | Steinbacher et al. | |
| 5,610,592 | A | 3/1997 | Okazaki | |
| 6,285,291 | B1 | 9/2001 | Knox et al. | |
| 6,773,489 | B2 * | 8/2004 | Dunn | B03C 3/36 209/127.1 |
| 7,669,457 | B2 | 3/2010 | Griffith et al. | |
| 8,603,262 | B2 * | 12/2013 | Lambert | B03C 3/025 134/104.2 |
| 2002/0134238 | A1 * | 9/2002 | Conrad | A47L 9/122 95/79 |
| 2003/0032694 | A1 * | 2/2003 | Meyer | C08L 71/02 523/122 |
| 2007/0209338 | A1 * | 9/2007 | Conrad | A47L 5/28 55/345 |
| 2008/0250926 | A1 * | 10/2008 | Riskin | B03C 3/06 95/57 |
| 2009/0025453 | A1 * | 1/2009 | Griffith | G08B 17/10 73/31.02 |
| 2010/0039645 | A1 | 2/2010 | Kemal | |
| 2012/0325084 | A1 * | 12/2012 | Sexton | G01N 1/2813 95/10 |

FOREIGN PATENT DOCUMENTS

| | | |
|---|---|---|
| JP | 07-44783 A | 2/1995 |
| WO | WO-1997/035287 A1 | 9/1997 |
| WO | WO-2011106840 A1 | 9/2011 |

OTHER PUBLICATIONS

Brown, Richard C., et al. "Electret-based passive dust sampler: sampling of organic dusts." Analyst 121.9 (1996): 1241-1246.*
Brown, R. C., et al. "Theory and measurement of the capture of charged dust particles by electrets." Journal of aerosol science 25.1 (1994): Abstract.*
"International Application No. PCT/AU2011/000237, International Search Report and Written Opinion dated May 25, 2011", (dated May 25, 2011), 12 pgs.
"European Application Serial No. 11750087.6, Office Action dated Oct. 12, 2012", 2 pgs.
"European Application Serial No. 11750087.6, Partial Supplementary European Search Report dated May 28, 2015", 5 pgs.
"European Application Serial No. 11750087.6, Response filed Apr. 3, 2013 to Office Action dated Oct. 12, 2012", 10 pgs.
"International Application No. PCT/AU2011/000237, International Preliminary Report on Patentability dated Sep. 11, 2012", 8 pgs.
"European Application No. 11750087.6, Extended European Search Report dated Apr. 7, 2016", (dated Apr. 7, 2016), 16 pgs.

* cited by examiner

PARTICLE PRECIPITATOR

PRIORITY CLAIM TO RELATED APPLICATIONS

This application is a national stage application under 35 U.S.C. § 371 of PCT/AU2011/000237, filed Mar. 3, 2011, and published as WO 2011/106840 A1 on Sep. 9, 2011, which claims priority to Australian Application No. 2010900937, filed Mar. 5, 2010, which applications and publication are incorporated by reference as if reproduced herein and made a part hereof in their entirety, and the benefit of priority of each of which is claimed herein.

FIELD OF THE INVENTION

The present invention relates to a particle precipitator employed in a sensing system for detecting particles in an airflow. More particularly, although not exclusively, the invention relates to an aspirating smoke detector, however the invention is not limited to this particular application and other types of sensing systems for detecting particles in an airflow are included within the scope of the present invention.

BACKGROUND OF THE INVENTION

Smoke detection systems can be falsely triggered by exposure to dust. In aspirating smoke detection systems, various analytical solutions have been implemented in order to detect the dust and thereby avoid a false alarm. In light-scatter-based smoke detection systems, dust discrimination or rejection may be implemented by using time-amplitude analysis (dust tends to produce a spike in the scatter signal) or by using multiple light wavelengths, multiple polarisations, multiple viewing angles, inertial separation, or combinations of the above. These analytical tools can unnecessarily complicate the smoke detection systems.

In order to avoid or reduce the problems associated with dust it is advantageous to limit the introduction of dust into the analysis site. This is typically performed by use of a foam, HEPA, or other mechanical filter. However, over time such filters may block, increasing resistance to air flow and extreme cases may even prevent smoke particles reaching the detection chamber.

It is therefore an object of the present invention to provide an improved particle separation system.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In accordance with a first aspect of the present invention, there is provided a particle separation system for separating particles in an airflow upstream of a detection chamber in an aspirating smoke detector, the particle separation system including an airflow path for directing the airflow from an inlet to an outlet, the airflow path including:
 a first airflow path section in a first direction and a second airflow path section in a second direction, the first and second directions being different relative to each other; and
 at least one electrically charged surface such that the airflow undergoes electrostatic precipitation as it traverses the airflow path.

Advantageously, the first and second airflow path sections are arranged relative to each other such that a bend or curve is formed in the airflow path where the two sections meet, and the airflow is caused to travel around the bend or curve as it moves from the inlet to the outlet. The intersection between the first airflow path section and the second airflow path section may include a transition region between the first and second directions.

In a preferred embodiment, the first and second airflow path sections are arranged at substantially 90° to each other in order to introduce a sharp bend into the airflow path. Other forms of bends or curves are envisaged by the invention.

Preferably the electrically charged surface is located downstream and adjacent the transition region between the first and second directions. Advantageously the electrically charged surface is located on the outside of the bend or curve such that larger particles are carried closer to the charged surface by their momentum as they traverse the bend or curve.

The electrically charged surface preferably takes the form of a substantially smooth surface and may form a wall of the airflow path. Alternatively, the electrically charged surface is folded, corrugated, textured, or similar in order to present a greater surface area to the airflow so as to attract more particles.

The first aspect of the invention also provides a method for separating particles in an airflow upstream of a detection chamber in an aspirating smoke detector, the method including:
 directing the airflow along a first airflow path section in a first direction and then along a second airflow path section in a second direction, wherein the first direction and second direction are different relative to each other; and
 providing at least one electrically charged surface within the airflow path such that the airflow undergoes electrostatic precipitation as it traverses the airflow path.

Advantageously, the method includes locating the electrically charged surface downstream and adjacent a transition region between the first and second directions.

In a second aspect of the invention there is provided a particle separation system for separating particles in an airflow upstream of a detection chamber in an aspirating smoke detector, the particle separation system including:
 a particle separation chamber having a first volume;
 an inlet airflow path for introducing the airflow into the particle separation chamber; and
 an outlet airflow path for exiting the airflow from the particle separation chamber;
 wherein the inlet and outlet airflow paths have volumes smaller than the first volume such that the airflow introduced into the particle separation chamber is caused to rapidly expand in a first region; and
 wherein the particle separation chamber includes one or more electrically charged surfaces adjacent the first region.

Preferably, the one or more electrically charged surfaces are in the form of plates that may also form one or more walls of the chamber. Alternatively, the electrically charged surfaces may be folded, corrugated, textured, or similar in order to present a greater surface area to the airflow so as to attract more particles.

Advantageously, the particle separation chamber is an electrostatic precipitation chamber.

In a further embodiment of the second aspect of the invention, the particle separation chamber further includes a barrier or wall means located in front of and near the inlet airflow path such that as the airflow is introduced into the chamber it is caused to diverge around the barrier or wall means. Advantageously, the barrier is located in such a position to cause eddies to develop in the airflow. In this manner the airflow cycles in the chamber bringing it into contact with the one or more electrically charged surfaces several times.

The second aspect of the invention also provides a method for separating particles in an airflow upstream of a detection chamber in an aspirating smoke detector, the method including:

introducing the airflow into a particle separation chamber;
causing the airflow to undergo a rapid expansion within the particle separation chamber in a first region;
providing one or more electrically charged surfaces adjacent the first region for attracting larger particles out of the airflow; and
exiting the airflow from the particle separation chamber.

Advantageously, the method further includes providing a barrier within the particle separation chamber to create eddies in the airflow and increase contact of the airflow with the one or more electrically charged surfaces.

In aspects of the invention described above, the electrically charged surface may be an electret material (polarised polymer), an actively charged surface relying on a high-voltage source to maintain the surface potential, or the charge may be intrinsic in the surface itself. For example, the charge may be intrinsic in the manufacture of the pipe or duct through which the airflow flows. In particular, electrically charged regions can develop during the plastics moulding process and the desired electrostatic field may be obtained without the need for a separate charged surface.

The applicant has further observed that the efficiency of particle removal from the airflow can diminish over time, generally due to the accumulation of particulate material on the electrically charged surfaces.

In a third aspect the invention accordingly provides a detection system for detecting particle accumulation in a particle separation system, the particle separation system including one or more electrically charged surfaces, the one or more electrically charged surfaces being at least partially transparent, the detection system including:

a light source for directing light towards at least one of the electrically charged surfaces; and a receiver for detecting the intensity of the light transmitted through or reflected from the at least one electrically charged surface.

The third aspect of the invention also extends to a method of detecting particle accumulation in a particle separation system, the particle separation system including one or more electrically charged surfaces, the one or more electrically charged surfaces being at least partially transparent, the method including providing a light source and directing light towards at least one of the electrically charged surfaces;

providing a receiver and detecting the intensity of the light transmitted through the at least one electrically charged surface;

obtaining two or more measurements of the intensity of light transmitted over time;

comparing the two or measurements of the intensity of light transmitted and determining from the comparison if the intensity of light transmitted has reduced over time.

The invention further provides a method of detecting particle accumulation in a particle separation system, the particle separation system including one or more electrically charged surfaces, the one or more electrically charged surfaces being at least partially transparent, the method including providing a light source and directing light towards at least one of the electrically charged surfaces;

providing a receiver and detecting the intensity of the light reflected from the at least one electrically charged surface;

obtaining two or more measurements of the intensity of light reflected over time;

comparing the two or measurements of the intensity of light reflected and determining from the comparison if the intensity of light reflected has increased over time.

In a further aspect of the invention there is provided a detection system for detecting particle accumulation in a particle separation system, the particle separation system including one or more electrically charged surfaces, the detection system including:

an acoustic transducer to mechanically excite vibration in at least one of the electrically charged surfaces; and a detector for measuring the intensity of damping or resonance of the at least one electrically charged surface.

There is also provided a method of detecting particle accumulation in a particle separation system, the particle separation system including one or more electrically charged surfaces, the method including providing an acoustic transducer and mechanically exciting vibration in at least one of the electrically charged surfaces;

providing a detector and measuring the intensity of damping of the at least one electrically charged surface;

obtaining two or more measurements of the intensity of damping over time;

comparing the two or measurements of the intensity of damping and determining from the comparison if the damping has increased over time.

There is also provided a method of detecting particle accumulation in a particle separation system, the particle separation system including one or more electrically charged surfaces, the method including providing an acoustic transducer and mechanically exciting vibration in at least one of the electrically charged surfaces;

providing a detector and measuring the intensity of resonance of the at least one electrically charged surface;

obtaining two or more measurements of the intensity of resonance over time;

comparing the two or measurements of the intensity of resonance and determining from the comparison if the resonance has reduced over time.

In a preferred embodiment, the acoustic transducer may be the electrically charged surface itself. Alternatively, the electrically charged surface may consist of a piezoelectric material, such as PVDF, which allows for both the provision of a charged surface and for exciting the surface acoustically.

In all aspects of the invention, the particle separation systems and detection systems described above may form part of a sensing system for detecting particles in an airflow.

The sensing system may include a detector to which the airflow flows for testing. The detector may be in the form of a particle detector such as a light-scatter particle detector. Preferably, the particle detector is a smoke detector. Suitably, the detector is connected to the fire alarm loop and optionally, to an appropriate suppressant system. A fan may be included in the particle separation system to induce air flow through the system.

In particularly preferred embodiments, the particle separation systems and detection systems described above are located upstream of a detection chamber of an aspirating smoke detector.

BRIEF DESCRIPTION OF THE DRAWINGS

Exemplary embodiments of the present invention will now be described by way of non-limiting example only, with reference to the accompanying drawings, in which.

DESCRIPTION OF PREFERRED EMBODIMENTS

Figure 1:
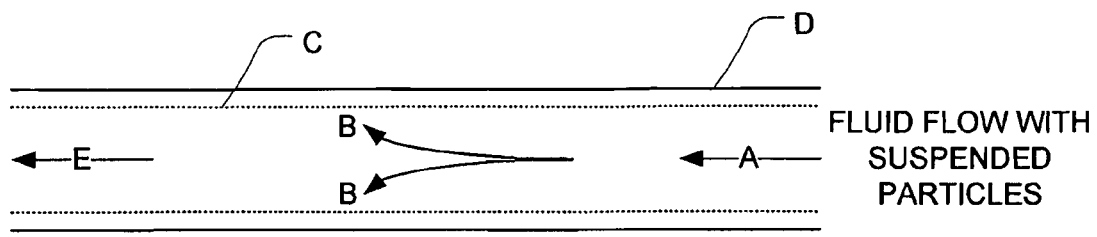
FIG. 1 illustrates an electrostatic precipitation chamber of an aspirating smoke detector according to a first preferred embodiment of the invention.

FIG. 1 illustrates the operation of an electrostatic precipitation chamber located upstream of a detection chamber (not shown) of an aspirating smoke detector (not shown). The airflow entering the electrostatic precipitation chamber generally contains a range of particles—larger particles, generally associated with dust rather than smoke, and smaller particles which are generally associated with smoke. In an aspirating smoke detector, the object of the electrostatic precipitation chamber is to preferentially attract the larger particles out of the airflow leaving the smaller particles unaffected so that they can travel to the detection chamber of the smoke detector.

Referring to FIG. 1, the air flow A containing suspended particles enters a pipe region D. Electrically charged surfaces C attract particulates B out of the flow resulting in an outflow E with a reduced particle content. The electrostatic field may be passively or actively generated and may be adjusted such that larger particles are preferentially drawn out of the airflow leaving relatively smaller particles to continue in outflow E.

In alternative, more complex embodiments the inventors have realised that inertial separation techniques can be combined with electrostatic filtration techniques to enhance performance of the system. In this regard, the airflow changed or path can be shaped, disturbed in such a way that heavy and light particles take different paths. In combination with this the electrostatic precipitator can be placed such that the heavy particles are more likely to be located closer to it, thus increasing the relative capture of the heavy particles.

Figure 2:
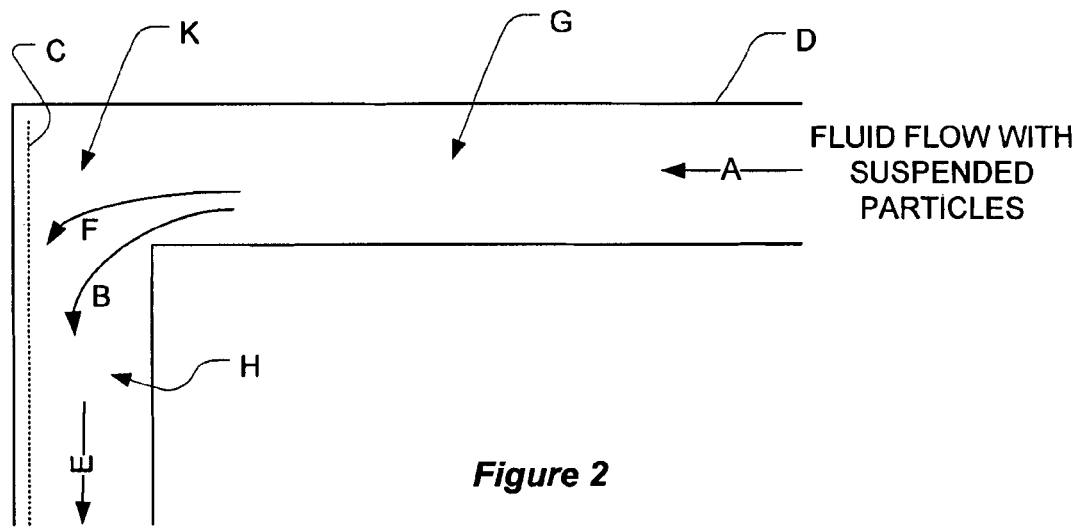
FIG. 2 illustrates a particle separation system according to second preferred embodiment of the present invention.

FIG. 2 illustrates a particle separation system according to a second embodiment of the invention. The particle separation system includes an airflow path defined by pipe D which further includes a first airflow section G and second airflow section H that are arranged at 90° to each other, thereby introducing a sharp bend K in the pipe D. The bend K forms a transition region between the first airflow section G and second airflow section H.

An electrically charged surface C is provided downstream and adjacent the transition region, and on the outside of the bend as illustrated. The electrically charged surface is a smooth surface and may form a wall of the pipe D.

Air flow with suspended particles A enters the pipe D at the inlet end, travels through pipe D and around the bend K. As indicated in FIG. 2, as the fluid flow A passes around the bend, the larger, heavier particles F tend to take a wider path around the bend as they are carried by their momentum and approach the electrically charged surface C and adhere to it while the lighter, smaller particles B follow the air stream more closely and exit the pipe D as part of the remaining flow E.

It will be appreciated that other forms of bends or curves may be utilised to alter the direction of travel of the airflow such that larger particles within the airflow come into close proximity to the electrically charged surface by virtue of their own momentum as the airflow travels around the bend or curve.

Figure 3:
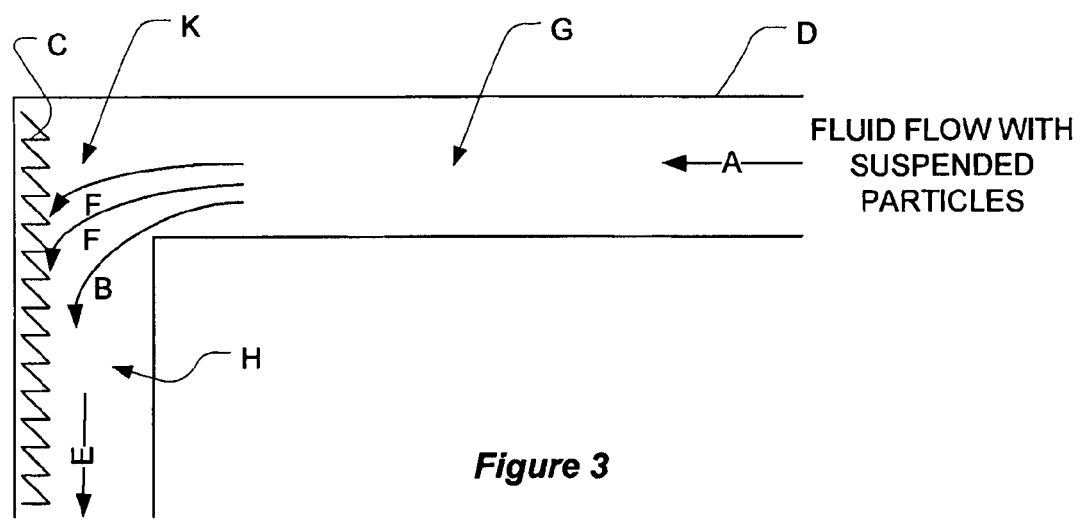
FIG. 3 illustrates an alternative embodiment of the particle separation system of FIG. 2.

FIG. 3 illustrates an alternate form of electrically charged surface C. In this embodiment the electrically charged surface C is folded in order to present a larger surface area to the air flow A. By increasing the surface area of the electrically charged surface C by folding, corrugating, or similarly texturing the surface, the number of particles intercepted by the charged surface C is increased.

Figure 4:
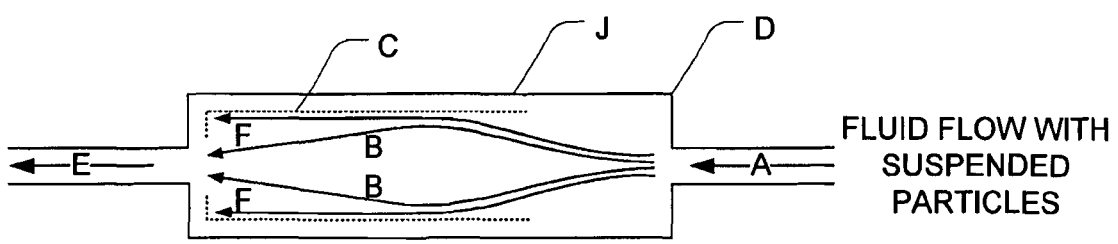
FIG. 4 illustrates a particle separation system according to a third preferred embodiment of the present invention.

A further embodiment of a particle separation system is illustrated in FIG. 4. Air flow with suspended particles A enters via a relatively small dimension inlet into chamber J where the air flow undergoes a rapid expansion in region H before contracting again to leave the chamber via an outlet which is also of relatively small dimension. Electrically charged surfaces C are located within the chamber and preferably line the perimeter walls. Most preferably the electrically charged surfaces C are located adjacent the region of rapid expansion and towards the outlet.

Smaller particles B follow the streamlines more readily and leave the chamber J as part of the exit stream E. Larger, heavier particles F lag the air stream motion and as a result are more likely to approach the electrically charged surfaces C to which they will adhere.

Figure 5:
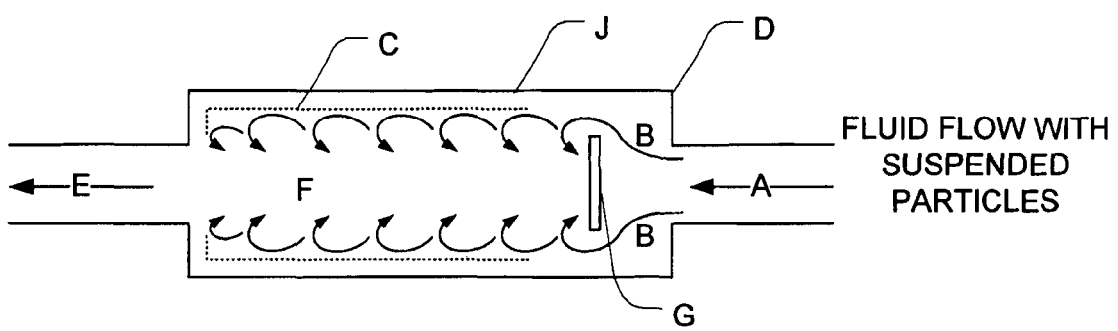
FIG. 5 illustrates an alternative embodiment of the particle separation system of FIG. 4.
Figure 6:
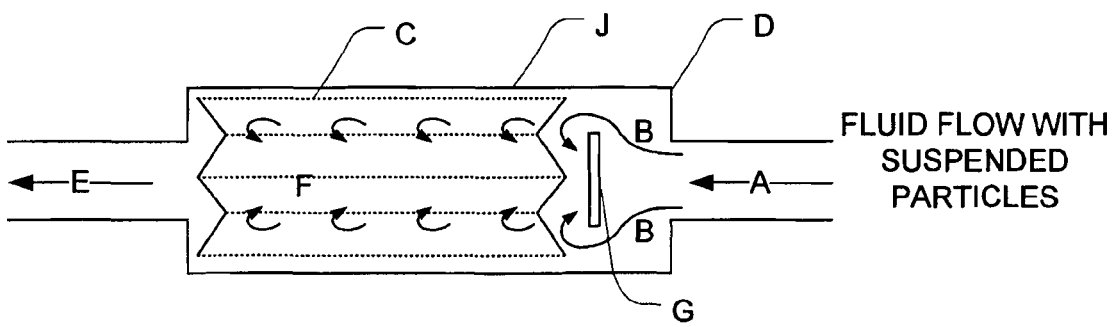
FIG. 6 illustrates a further alternative embodiment of the particle separation system of FIG. 4.

Further variations to the system of FIG. 4 are illustrated in FIGS. 5 and 6. In FIG. 5 a barrier G is placed in front of the entering air flow A. The air stream diverges to move around the barrier causing eddies to develop. This brings the air stream, and consequently the particles suspended therein, to cycle into close contact with the electrically charged surfaces C several times, thus increasing the likelihood of suspended particles adhering to the charged surfaces C. The larger heavier particles are more likely to be at the periphery of the eddies due to centrifugal acceleration and are therefore preferentially removed from the air stream.

Referring to FIG. 6, the capture of larger, heavier particles is enhanced by increasing the area of the charged surface C that is exposed to the air stream. In the illustrated configuration, the electrically charged surface C is constructed as a folded arrangement. Eddies in the air stream cycle while in close proximity to the extended surface area of C and the charged surface is therefore more effective in removing suspended particles. Due to the cyclic nature of the eddies and the centrifugal acceleration arising therefrom, larger, heavier particles are preferentially removed during the traversal of the electrically charged surface C.

It will be appreciated that there are variations on the configurations illustrated, involving more elaborate structures designed to direct the heavier, larger particles onto or near the electrically charged surface.

In a further preferred embodiment the electrically charged surface is an electret material (polarised polymer), or an actively charged surface relying on a high-voltage source to maintain the surface potential. Alternatively, the electric charge may be intrinsic in the manufacture of the pipe or duct through which the air flows. Electrically charged regions can develop during the plastic moulding process and the appropriate choice of material and moulding technique may be sufficient to produce the desired electrostatic field avoiding the need for a separate charged surface.

It has been observed, as is expected, that the efficiency of removal of particles from the air flow diminishes over time as the charged surface accumulates particulate material. It is therefore advantageous to incorporate a detection system that can determine the amount of material accumulated in order to signal the need for replacement or cleaning of the charged surface.

In a further embodiment of the invention, the charged surfaces are made of a transparent or partially transparent material, and the detection system employs parameters such as the reflection of light from or transmission of light through the charged surface. Such parameters vary over time and are used to indicate the need for replacement or other maintenance.

Figure 7:
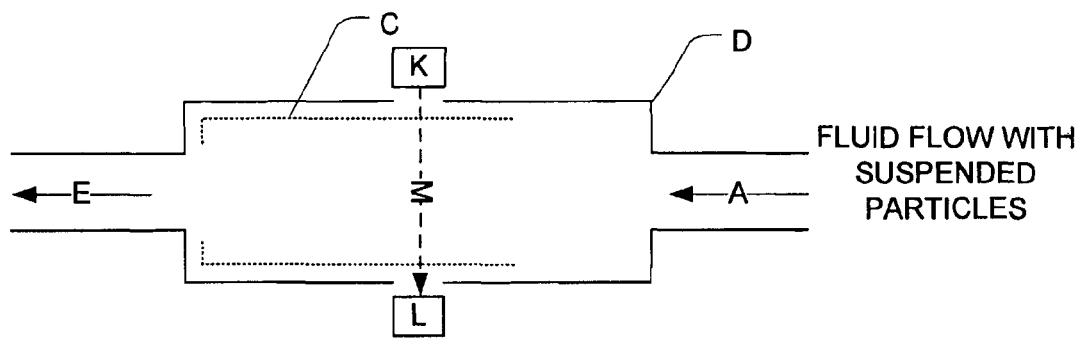
FIG. 7 illustrates a detection system according to a fourth preferred embodiment of the present invention.
Figure 8:
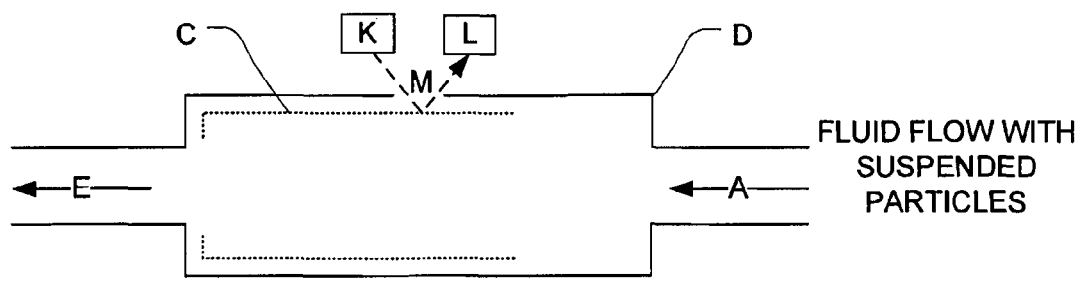
FIG. 8 illustrates an alternative embodiment of the detection system of FIG. 7.

A detection system as envisaged above is shown in FIGS. 7 and 8. In FIG. 7 a light source K transmits light M though a transparent charged surface C to receiver L. As the surface C becomes contaminated the received light intensity at receiver L is reduced.

Similarly in FIG. 8. A light source K transmits light onto the transparent charged surface C. Some of the light M is received by the receiver L. The amount of light so reflected depends on the amount of particulate on the surface C and so this can be used to indicate that maintenance is required.

A similar method of detecting accumulated material on the charged surfaces involves using an acoustic transducer to excite the charged surface acoustically and measure parameters such as resonance and damping.

Figure 9:
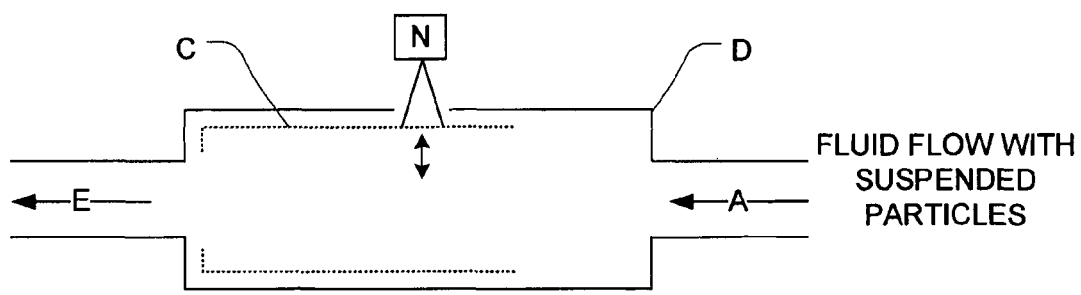
FIG. 9 illustrates a detection system according to a further embodiment of the present invention.

As shown in FIG. 9, acoustic transducer N is used to mechanically excite vibration in the charged surface C. Measurement of damping or resonance indicate the extent to which mass is adhering to the charged surface C.

In some embodiments the transducer used may be the charged surface itself. For example, an electrostatic loudspeaker may be made by placing a charged surface between electrodes and varying the voltage between the parts of the surface or electrode structure. In another variation, the charged material may be made of a piezoelectric material, such as PVDF which will allow for both maintaining a charged surface and for exciting the surface acoustically.

It will be understood that any of the optical or acoustic parameters described above, either singly or in combination may be useful in determining the extent of material adhering to the charged surface and therefore the need for maintenance.

It will be appreciated that the preferred embodiments of the present invention provide improved particle separation systems resulting in improved particle separation and therefore dust rejection. Particle separation systems as described incorporated in smoke detection systems reduce the likelihood of false alarms triggered by exposure to dust for a given alarm level setting.

In a preferred embodiment, a particle separation system is incorporated in an aspirated particle detection system (not illustrated). The particle detection system includes an inlet into which air is drawn from the volume being monitored. The airflow is drawn up the upper sample inlet to an electrostatic precipitation chamber. The electrostatic precipitation chamber may be of any of the types previously described in the specification. After traversing the electrostatic precipitation chamber, the air sample passes into a detection chamber. The detection chamber can, for example, be an optical particle detection chamber such as the one used in a "Vesda" air sampling smoke detector as produced by Xtralis Proprietary Limited. In such systems, a beam of light is shone across the air sample and scattered light is monitored by a light receiver to detect light scattered from particles in the airflow. The output of this detector is then processed by a smoke detection controller and alarm logic applied to determine if particles exist and whether an action needs to be taken in response to their detection. The particle detection system also includes an aspirator in the form of a fan which is used to draw air through the particle detection system. After traversing the particle detection system, the air is passed back to the atmosphere via an exhaust.

A further embodiment of a particle detection system is typically referred to as a sub-sampling particle detection system (not illustrated). In this regard, the sub-sampling particle detection system includes a primary airflow path in which an aspirator draws air from an inlet and out to an outlet. The airflow will typically be an air sample from a volume being monitored for the presence of particles. From this main airflow, a sub-sample is drawn via a sub-sampling path. The sub-sampling path is passed through an electrostatic precipitation chamber and then to a particle detection chamber. The particle detection chamber and electrostatic precipitation chamber can be the same as that described in the previous embodiment. Air from the sub-sampling path then rejoins the airflow main path.

Either of the aspirated or sub-sampling particle detection systems described above can be implemented in aspirated smoke detection systems (not illustrated). In one embodiment, the aspirated smoke detection system is coupled to a sampling pipe network which includes a plurality of sampling pipes arranged in a branched configuration. In each of the branches, there are a plurality of sample inlets or sampling holes. Air is drawn into the sampling holes through the pipe network to the particle detection system where the air samples are analysed to determine whether particles exist. As will be appreciated by those skilled in the art the various branches of the particle detection network may be used to monitor different air volumes (such as rooms) within a premises.

The foregoing describes preferred embodiments of the present invention and modifications may be made thereto without departing from the scope of the invention. It will be understood that the invention disclosed and defined in this specification extends to all alternative combinations of two or more of the individual features mentioned or evident from the text or drawings. All of these different combinations constitute various alternative aspects of the invention.

The invention claimed is:

1. A particle separation system for separating particles from an airflow in which they are entrained, at a position upstream of a detection chamber in an aspirating smoke detector, the particle separation system including an airflow path for directing the airflow from an inlet to an outlet, the airflow path including:

a first airflow path section in which the airflow passes in a first direction and a second airflow path section in which the airflow passes in a second direction, wherein the first and second directions are different relative to each other;

the intersection between the first airflow path section and the second airflow path section includes a transition region between the first and second directions; and the transition region includes a bend or curve where the two sections meet, and the airflow is caused to travel around the bend or curve as it moves from the inlet to the outlet; and at least one passively electrically charged surface located on the outside of said bend or curve downstream and adjacent the transition region and exposed to the airflow such that some particles in the airflow electrostatically adhere to the passively electrically charged surface as the airflow traverses the airflow path, whereby said adhered particles are separated from the airflow.

2. The particle separation system according to claim 1, wherein the electrically charged surface may be an electret material (polarized polymer), or the charge may be intrinsic in the surface itself.

3. A method for separating particles from an airflow in which they are entrained, at a position upstream of a detection chamber in an aspirating smoke detector, the method including:

using a particle separation system located upstream of the particle detection chamber of the aspirating smoke detector, directing the airflow along a first airflow path section in a first direction and then along a second airflow path section in a second direction, wherein the first direction and second direction are different relative to each other;

the intersection between the first airflow path section and the second airflow path section includes a transition region between the first and second directions;

the transition region includes a bend or curve where the two sections meet, and the airflow is caused to travel around the bend or curve as it moves from the inlet to the outlet; and a passively electrically charged surface is located downstream and adjacent the transition region between the first and second directions on the outside of said bend or curve; and exposing the passively electrically charged surface to the airflow path such that some particles in the airflow electrostatically adhere to the passively electrically charged surface as the airflow traverses the airflow path, whereby said adhered particles are separated from the airflow.

4. A particle separation system for separating particles from an airflow in which they are entrained, at a position upstream of a detection chamber in an aspirating smoke detector, the particle separation system including:

a particle separation chamber having a first cross section;

an inlet airflow path for introducing the airflow into the particle separation chamber; and an outlet airflow path for exiting the airflow from the particle separation chamber;

wherein the inlet and outlet airflow paths have cross sections smaller than the particle separation chamber such that the airflow introduced into the particle separation chamber is caused to rapidly expand, wherein said rapid expansion causes particles entrained in the airflow to reduce their speed;

wherein the particle separation chamber includes one or more passively electrically charged surfaces such that some particles in the airflow electrostatically adhere to the one or more passively electrically charged surfaces as the airflow traverses the airflow path, whereby said adhered particles are separated from the airflow;

wherein the passively electrically charged surface is folded, corrugated or textured in order to present a greater surface area to the airflow so as to attract more particles; and wherein within the particle separation chamber there is located a barrier or wall located in front of and near the inlet airflow path such that, as the airflow is introduced into the chamber, it is caused to diverge around the barrier or wall towards said at least one passively electrically charged surface.

5. The particle separation system according to claim 4, wherein the passively electrically charged surface may be an electret material (polarized polymer), or the charge may be intrinsic in the surface itself.

6. A method for separating particles from an airflow in which they are entrained, at a position upstream of a detection chamber in an aspirating smoke detector, the method including:

introducing the airflow into a particle separation chamber;

causing the airflow to undergo a rapid expansion within the particle separation chamber in a first region, wherein said rapid expansion causes the airflow to reduce its speed;

providing a barrier or wall within the first region of the particle separation chamber near an inlet to the particle separation chamber thereby causing divergence of the airflow around the barrier or wall;

exposing one or more passively electrically charged surfaces, located adjacent the first region, thereby attracting particles out of the airflow, such that some particles in the airflow electrostatically adhere to the passively electrically charged surface as the airflow traverses the airflow path, whereby said adhered particles are separated from the airflow, wherein the passively electrically charged surface is folded, corrugated or textured in order to present a greater surface area to the airflow so as to attract more particles; and exiting the airflow from the particle separation chamber.

* * * * *